(12) United States Patent
Iwaya et al.

(10) Patent No.: US 11,982,659 B2
(45) Date of Patent: May 14, 2024

(54) SYSTEM, METHOD AND PROGRAM FOR CALIBRATING MOISTURE SENSOR

(71) Applicant: Ball Wave Inc., Sendai (JP)

(72) Inventors: Takamitsu Iwaya, Sendai (JP); Shingo Akao, Sendai (JP); Tatsuhiro Okano, Sendai (JP); Nobuo Takeda, Sendai (JP); Toshihiro Tsuji, Sendai (JP); Toru Oizumi, Sendai (JP); Hideyuki Fukushi, Sendai (JP); Maki Sugawara, Sendai (JP); Yusuke Tsukahara, Sendai (JP); Kazushi Yamanaka, Sendai (JP)

(73) Assignee: Ball Wave Inc., Sendai (JP)

( * ) Notice: Subject to any disclaimer, the term of this patent is extended or adjusted under 35 U.S.C. 154(b) by 369 days.

(21) Appl. No.: 17/397,723

(22) Filed: Aug. 9, 2021

(65) Prior Publication Data

US 2021/0372978 A1 Dec. 2, 2021

Related U.S. Application Data

(63) Continuation of application No. PCT/JP2020/009893, filed on Mar. 6, 2020.

(Continued)

(51) Int. Cl.
*G01N 33/00* (2006.01)

(52) U.S. Cl.
CPC ..... *G01N 33/0008* (2013.01); *G01N 33/0036* (2013.01); *G01N 33/0062* (2013.01)

(58) Field of Classification Search
CPC ........... G01N 33/0006; G01N 27/4175; G01N 25/56; G01N 27/223; G01N 21/274; G01N 35/00693; G01N 27/121; G01N 25/60

(Continued)

(56) References Cited

U.S. PATENT DOCUMENTS 3,218,841 A * 11/1965 Lerner ................. G01N 27/223
                                                      73/1.02
3,290,920 A * 12/1966 Novak ................... G01N 21/91
                                                      73/1.03

(Continued)

FOREIGN PATENT DOCUMENTS

CN         105021674 A  * 11/2015
CN         103591976 B  *  8/2016

(Continued)

OTHER PUBLICATIONS

Extended European Search Report for EP Application No. 20769866.3, dated Jul. 13, 2022, 10 pages.

(Continued)

*Primary Examiner* — David A. Rogers
(74) *Attorney, Agent, or Firm* — Polsinelli PC

(57) ABSTRACT

A system for calibrating a moisture sensor encompasses a processing unit (341). The processing unit (341) includes a reference data obtaining LCKT (345), a subject data obtaining LCKT (346) and a relationship calculating LCKT (347). The reference data obtaining LCKT (345) obtains reference data, after injecting water-vapor with known concentrations into an analyzer. The subject data obtaining LCKT (346) measures subject data indicating temporal variation of output-responses of a subject sensor element of the analyzer under test. The relationship calculating LCKT (347) compares the subject data with the reference data, and calculates relationships between the output-responses of the subject sensor element and the known concentrations.

5 Claims, 14 Drawing Sheets

Related U.S. Application Data

(60) Provisional application No. 62/815,379, filed on Mar. 8, 2019.

(58) Field of Classification Search
USPC .................. 73/1.02, 1.06, 1.07, 25.04, 29.01
See application file for complete search history.

(56) References Cited

U.S. PATENT DOCUMENTS

| | | | |
|---|---|---|---|
| 3,894,419 A | 7/1975 | Mator et al. | |
| 3,916,367 A * | 10/1975 | Nicholas | G01N 27/121 200/61.04 |
| 4,218,746 A * | 8/1980 | Koshiishi | G01N 27/4165 204/406 |
| 4,481,596 A * | 11/1984 | Townzen | G01K 7/021 374/E7.016 |
| 5,343,747 A * | 9/1994 | Rosen | G01N 25/56 165/223 |
| 5,457,983 A * | 10/1995 | Sauvageau | G01N 33/0006 73/1.06 |
| 5,485,754 A | 1/1996 | Harpster | |
| 5,502,659 A | 3/1996 | Braster et al. | |
| 5,648,605 A * | 7/1997 | Takahashi | G01F 25/13 73/197 |
| 5,922,939 A * | 7/1999 | Cota | G01N 27/225 73/866.5 |
| 6,286,375 B1* | 9/2001 | Ward | G01N 30/12 73/19.09 |
| 6,299,147 B1* | 10/2001 | Mitter | F24F 6/02 261/142 |
| 6,395,560 B1* | 5/2002 | Markelov | G01N 1/2226 422/89 |
| 6,581,435 B2* | 6/2003 | Wang | G01N 27/4163 73/1.02 |
| 7,484,399 B2* | 2/2009 | Wohltjen | G01N 1/2226 73/1.03 |
| 7,842,243 B2* | 11/2010 | Sarkisov | G01N 21/77 356/73.1 |
| 7,900,496 B2* | 3/2011 | Mayer | G01N 33/0006 73/1.06 |
| 8,148,691 B1* | 4/2012 | Wong | G01N 33/0006 250/252.1 |
| 10,349,873 B2* | 7/2019 | Kamath | A61B 5/1473 |
| 11,141,549 B2* | 10/2021 | Tolmie | A61M 16/12 |
| 11,754,305 B2* | 9/2023 | Nigg | G01N 33/0073 73/1.06 |
| 2010/0018288 A1 | 1/2010 | Yamanaka et al. | |
| 2013/0074575 A1 | 3/2013 | Duric et al. | |
| 2013/0160518 A1* | 6/2013 | Leneel | G01N 27/223 73/335.04 |
| 2019/0033275 A1 | 1/2019 | Sun | |
| 2019/0195820 A1* | 6/2019 | Fornasari | G01N 27/223 |

FOREIGN PATENT DOCUMENTS

| | | | |
|---|---|---|---|
| CN | 104122915 B * | 8/2016 | |
| CN | 111189889 A * | 5/2020 | ........... G01N 27/121 |
| DE | 102005017693 A1 | 10/2006 | |
| EP | 1 967 842 A2 | 9/2008 | |
| JP | 60-122371 A | 6/1985 | |
| JP | 2001-056325 A | 2/2001 | |
| JP | 2004198396 A * | 7/2004 | |
| JP | 2005118760 A * | 5/2005 | |
| JP | 2007-263877 A | 10/2007 | |
| JP | 2009-543070 A | 12/2009 | |
| JP | 2015-004613 A | 1/2015 | |
| KR | 900005040 Y1 * | 6/1990 | |
| KR | 101647228 B1 * | 8/2016 | |
| RU | 2189033 C2 * | 9/2002 | |
| WO | 2008005907 A2 | 1/2008 | |
| WO | 2008005907 A3 | 1/2008 | |
| WO | WO 2008/056458 A1 | 5/2008 | |

OTHER PUBLICATIONS

N. Takeda et al.; "Deep Sub-micro Water-Vapor Measurement by Dual-Ball SAW Sensors for Temperature Compensation"; Spring Science + Business Media ; Aug. 23, 2015; 13 pages.

English translation for DE 10 2005 017 693A1, 6 pages.

International Search Report and Written Opinion, dated Jun. 23, 2020, for the corresponding International Application No. PCT/JP2020/009893 in 7 pages.

Hisashi Abe, et al., "Development of humidity standard in trace-moisture region: Characteristics of humidity generation of diffusion tube humidity generator", Elsevier, available online at www.sciencedirect.com on Feb. 13, 2006 in 7 pages.

Hisashi Abe, et al., "Improvement of flow and pressure controls in diffusion-tube humidity generator: Performance evaluation of trace-moisture generation using cavity ring-down spectroscopy", Elsevier, available online at www.sciencedirect.com on Dec. 20, 2006 in 7 pages.

English Abstract of Japanese application No. JP 2009-543070, retrieved on Jun. 2, 2023, 13 pages.

Korean Office Action for KR application No. 10-2021-7026976, dated May 16, 2023, 4 pages.

* cited by examiner

SYSTEM, METHOD AND PROGRAM FOR CALIBRATING MOISTURE SENSOR

CROSS-REFERENCE TO RELATED APPLICATIONS

This application is a continuation of International Application No. PCT/JP2020/009893, filed on Mar. 6, 2020, which claims the priority benefit to U.S. Application No. 62/815,379, filed Mar. 8, 2019, the entire contents of which are incorporated by reference.

TECHNICAL FIELD

The present invention related to a system, a method and a program for realizing on-site calibration of moisture sensor.

BACKGROUND ART

In the process of manufacturing semiconductors and materials that react easily with water, moisture analyzers are used for controlling trace moisture in the process gases as recited in non-patent literature (NPL) 1, and on-site calibration is required to achieve the reliability. Generally, the calibration is performed where the output-response to trace moisture has reached a sufficient equilibrium by maintaining the moisture concentration in the sensor cell for several hours (NPL2).

However, while such static calibration method enables accurate calibration, it is difficult to apply the static calibration method to on-site calibration because the calibration system is huge and the calibration takes as long as ten hours. In addition, since the earlier calibration system needs a large amount of calibration gases, it is difficult to apply it to processes using special gases for which there is no existing calibration system, or it is not easy to obtain a large amount of calibration gases.

CITATION LIST

Non Patent Literature

[NPL 1]: H. Abe et al.: Sens. Actu. A 128, 202-208 (2006).
[NPL 2]: H. Abe et al.: Sens. Actu. A 136, 723-729 (2007).

SUMMARY OF INVENTION

Technical Problem

In view of the above problems, an object of the present invention is to provide a system, a method and a program for calibrating a moisture sensor, which can be performed in a short time and are applicable to on-site calibrations.

Solution to Problem

The first aspect of the present invention inheres in a system for calibrating a moisture sensor encompassing a processing unit. The processing unit pertaining to the first aspect includes (a) a logic circuit configured to obtain reference data, which indicate temporal variation of moisture concentrations, after injecting water-vapor with known concentrations into an analyzer, (b) a logic circuit configured to measure subject data indicating temporal variation of output-responses of a subject sensor element of the analyzer under test, the subject data are obtained under same condition with the reference data was obtained, (c) a logic circuit configured to compare the subject data with the reference data, with same time-duration for obtaining the reference data, the time-duration is measured from a timing at which the water-vapor with the known concentrations is injected for calculating relationships between the output-responses of the subject sensor element and the known concentrations.

The second aspect of the present invention inheres in a method for calibration of moisture sensor, including (a) obtaining reference data, which indicate temporal variation of moisture concentrations, after injecting water-vapor with known concentrations into an analyzer of a calibration system, (b) measuring subject data indicating temporal variation of output-responses of a subject sensor element of the analyzer under test, the subject data are obtained under same condition with the reference data was obtained, (c) comparing the subject data with the reference data, with same time-duration for obtaining the reference data, the time-duration is measured from a timing at which the water-vapor with the known concentrations is injected, and (d) calculating relationships between the output-responses of the subject sensor element and the known concentrations.

The third aspect of the present invention inheres in a non-transitory computer readable storage medium storing a calibration program of system for calibrating a moisture sensor, the calibration program causing a processing unit in the system to execute processing for calibration by a series of instructions for performing calibration. The series of instructions pertaining to the third aspect encompasses (a) obtaining reference data, which indicate temporal variation of moisture concentrations, after injecting water-vapor with known concentrations into an analyzer of a calibration system, (b) measuring subject data indicating temporal variation of output-responses of a subject sensor element of the analyzer under test, the subject data are obtained under same condition with the reference data was obtained, (c) comparing the subject data with the reference data, with same time-duration for obtaining the reference data, the time-duration is measured from a timing at which the water-vapor with the known concentrations is injected, and (d) calculating relationships between the output-responses of the subject sensor element and the known concentrations.

Advantageous Effects of Invention

According to the present invention, it is possible to provide the system, the method and the program for calibrating the moisture sensor, which can be performed in a short time and are applicable to the on-site calibrations.

DESCRIPTION OF EMBODIMENTS

Illustrative Example

Before describing first and second embodiments of the present invention, with reference to FIGS. 3, 4, 5A and 5B, we will introduce an illustrative example for static calibration system, which has led to the first and second embodiments of the present invention.

Figure 4:
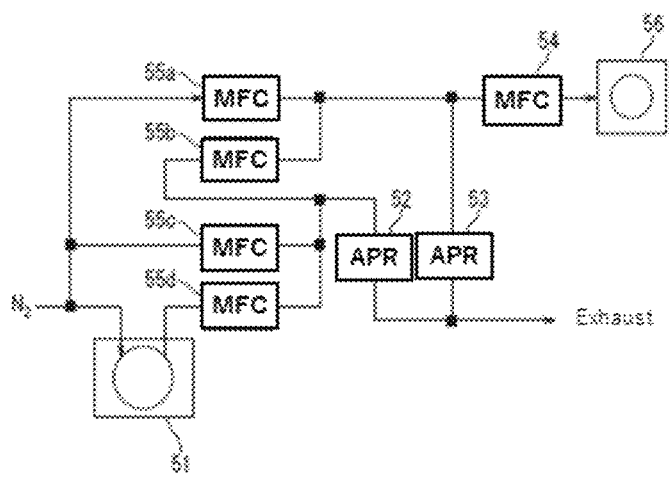
FIG. 4 is a schematic view illustrating an outline of a static calibration system pertaining to an illustrative example.

As illustrated in FIG. 4, a static calibration system pertaining to the illustrative example includes a first mass flow controller (MFC) 55a, a second MFC 55b, a third MFC 55c, a fourth MFC 55d, a fifth MFC 54, a first automatic pressure regulator (APR) 52 and a second APR 53 so as to implement a wet gas line through the fourth MFC 55d, a first dry gas line through the first MFC 55a and a second dry gas line through the third MFC 55c. The second dry gas line and the wet gas line are connected to implement a first mixed gas line through the second MFC 55b. The first dry gas line and the first mixed gas line are connected to implement a second mixed gas line through the fifth MFC 54. The first mixed gas line is branched to an exhaust gas line through the first APR 52.

The exhaust gas line and the second mixed gas line are bypassed by a pressure control line through the second APR 53. The moisture concentration around the calibrating sensor 56 can be changed by controlling the flow ratio between the wet gas line through a saturator 51 and the first and second dry gas lines and the first mixed gas line. The saturator 51 is a ¼ inch stainless steel pipe containing pure water and introduces a constant concentration of saturated water-vapor by controlling the temperature with a Peltier device.

Figure 5:
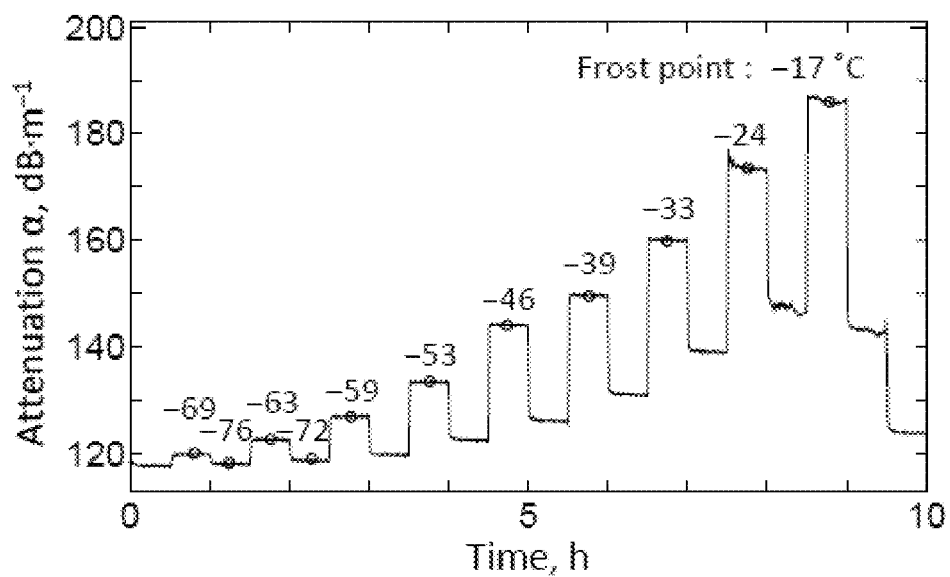
FIG. 5 is a diagram illustrating an example of the sensor response when the moisture concentration is changed stepwise using the static calibration system pertaining to the illustrative example.

FIG. 5 is an example of the sensor response when the moisture concentration is changed stepwise using the system illustrated in FIG. 4. The graph illustrated in FIG. 5 illustrates the temporal variation of the attenuation Alpha [GREEK] as the output-response of the ball SAW sensor in ten hours when the moisture concentration evaluated as the frost point (FP) was changed in steps from −76 degrees centigrade to −17 degrees centigrade. From the data illustrated in FIG. 5, a calibration curve of the relationship between the FP and the attenuation Alpha can be obtained. While the system illustrated in FIG. 4 is capable of accurate calibration, it is too huge to apply to on-site calibration.

Figure 6A:
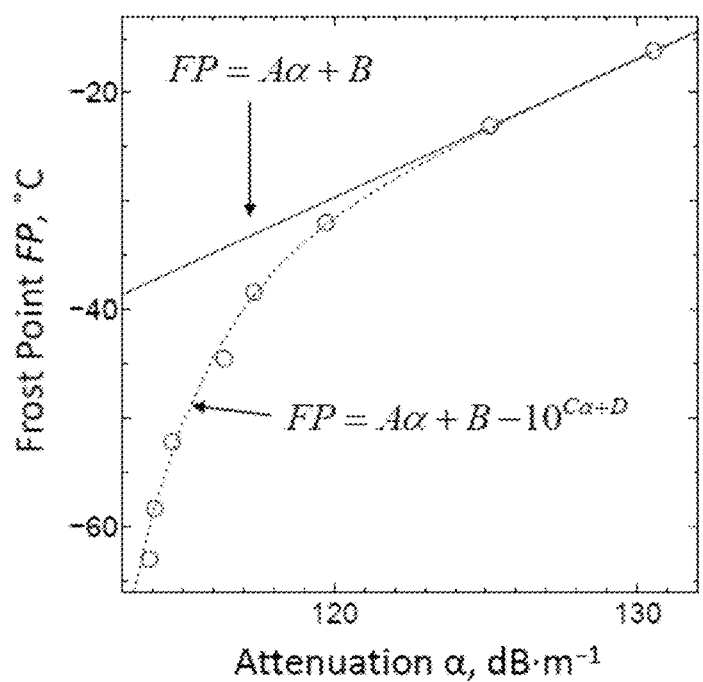
FIG. 6A is a diagram illustrating relationship between output-response as the attenuation Alpha[GREEK] of a ball SAW sensor and moisture concentration equivalent to frost point (FP) obtained by the static calibration system pertaining to the illustrative example.

In FIG. 6A, the relationships between the FP and the attenuation Alpha of the ball SAW sensor, which are obtained by the static calibration system illustrated in FIG. 4, are plotted as open circles. In FIG. 6A, we found that the relationship indicated as a dotted curve can be expressed as a function of the attenuation Alpha given by

[Math. 1]

$$FP = A\alpha + B - 10^{C\alpha + D}, \quad (1)$$

where A, B, C, and D are coefficients, which are characteristics of each sensor.

That is, the calibration of the ball SAW sensor means the determination of the coefficients A, B, C, and D. When the FP is above −25 degrees centigrade, the FP can be approximated to be almost linear to the attenuation Alpha neglecting the exponential term of Eq. (1) as

[Math. 2]

$$FP = A\alpha + B. \quad (2)$$

Therefore, the coefficients A and B can be determined by a least squares fitting of the data in the high concentration range. Furthermore, Eq. (1) can be transformed to

Figure 6B:
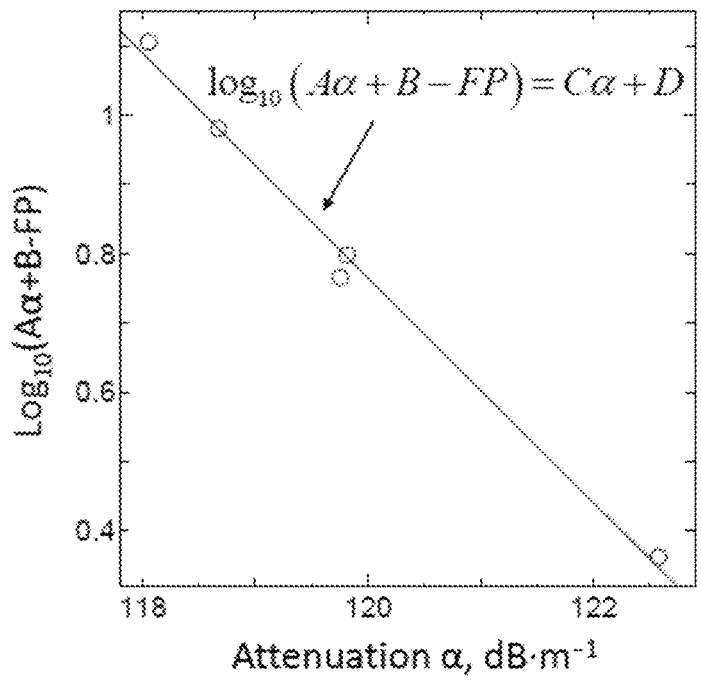
FIG. 6B is a diagram illustrating relationship between the attenuation Alpha and FP in the low concentration range.

[Math. 3]

$$\log_{10}(A\alpha + B - FP) = C\alpha + D, \quad (3)$$

expressing the exponential term of Eq. (1) as a linear function. FIG. 6B illustrates the relationship between the attenuation Alpha and the values on the left-hand side of Eq. (3) using data in the low FP range.

Therefore, the coefficients C and D can be determined by a least squares fitting. By using the coefficients A, B, C, and D, we can obtain the calibration curve for the sensor as

[Math. 4]

$$FP = 1.279\alpha - 182.8 - 10^{-0.1776\alpha + 21.56}. \quad (4)$$

First Embodiment

Now, embodiments of the present invention will be described below with reference to the drawings. In the descriptions of the following drawings, the same or similar reference numerals are assigned to the same or similar portions. However, the drawings are diagrammatic, and attention should be paid to a fact that the relations between thicknesses and plan view dimensions, the configuration of the apparatus and the like differ from the actual data. Thus, the specific thicknesses and dimensions should be judged by considering the following descriptions.

Also, even between the mutual drawings, the portions in which the relations and rates between the mutual dimensions are different are naturally included. Also, the embodiment as described below exemplify the apparatuses and methods for embodying the technical ideas of the present invention, and in the technical ideas of the present invention, the materials, shapes, structures, arrangements and the like of configuration parts are not limited to the followings.

In the following description, the "horizontal" direction or the "vertical" direction is simply assigned for convenience of explanation and does not limit the technical spirit of the present invention. Therefore, for example, when the plane of paper is rotated 90 degrees, the "horizontal" direction is changed to the "vertical" direction and the "vertical" direction is changed to the "horizontal" direction. When the plane of paper is rotated 180 degrees, the "left" side is changed to the "right" side and the "right" side is changed to the "left" side. Therefore, various changes can be added to the technical ideas of the present invention, within the technical scope prescribed by claims.

System Configuration

Figure 1A:
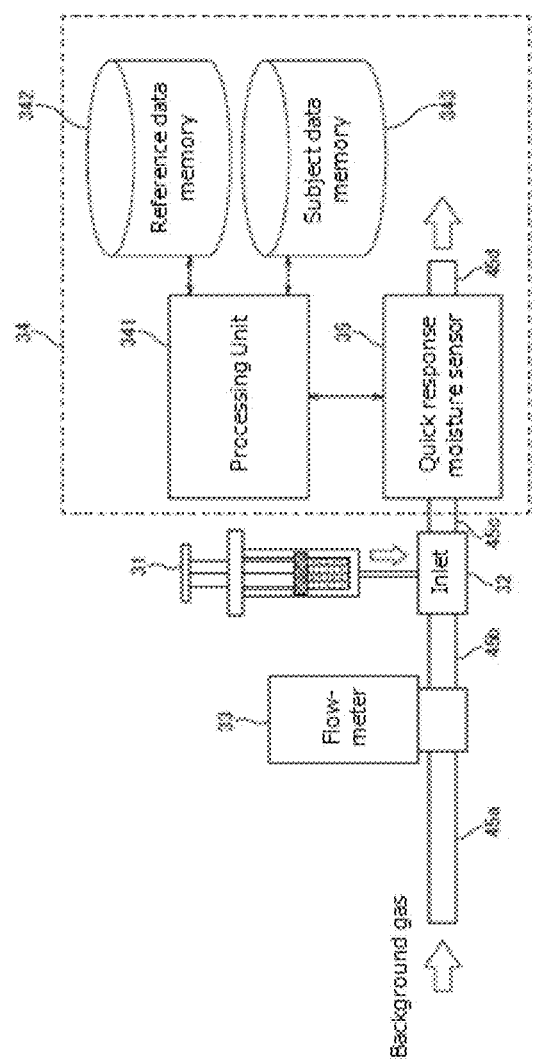
FIG. 1A is a conceptual diagram of a dynamic calibration system pertaining to a first embodiment of the present invention.

As illustrated in FIG. 1A a calibration system pertaining to a first embodiment of the present invention encompasses, a first pipe 45a through which background gas flows, a flowmeter 33 installed between the first pipe 45a and a second pipe 45b, an inlet 32 installed between the second pipe 45b and a third pipe 45c, an injector 31 for injecting a constant volume of the calibration gas to the inlet 32, and a quick response moisture sensor 35 installed at downstream of the inlet 32 through the third pipe 45c, which serve as "an introduction pipe".

As illustrated in FIG. 1A, the calibration system pertaining to the first embodiment further encompasses a processing unit 341 connected to the moisture sensor 35, a reference data memory 342 connected to the processing unit 341, and a subject data memory 343 connected to the processing unit 341. The moisture sensor 35, the processing unit 341, the reference data memory 342 and the subject data memory 343 implement a moisture analyzer 34.

Figure 1B:
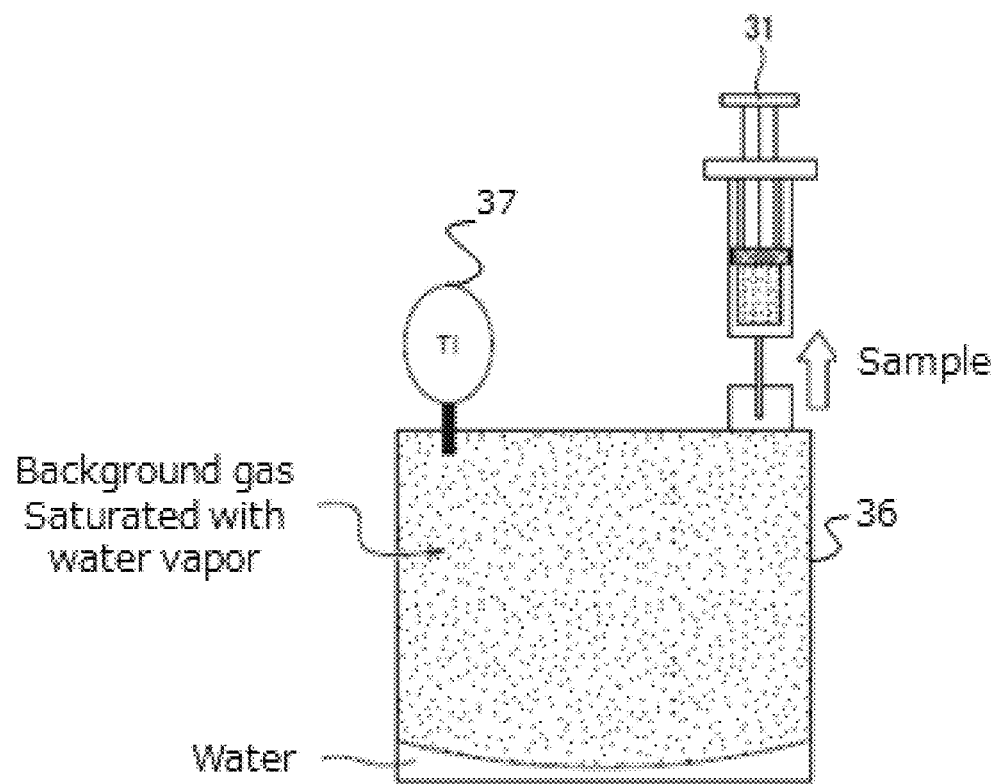
FIG. 1B is a conceptual diagram of saturated water-vapor generator used for the dynamic calibration system illustrated in FIG. 1A.

The water-vapor generator 36 illustrated in FIG. 1B produces saturated water-vapor in background gases on the head space provided above water, the water is contained in the lower portion of the water-vapor generator 36. At an upper portion of the water-vapor generator 36, a thermometer 37 is attached. The thermometer 37 measures temperature of the background gases saturated with water-vapor. Prior to conducting calibration with the calibration system illustrated in FIG. 1A, the tip of the injector 31 is supposed to be inserted in the water-vapor generator 36. And, by the injector 31, the saturated water-vapor is sampled from the water-vapor generator 36.

Thereafter, the background gas is introduced into the first pipe 45a illustrated in FIG. 1A, and the background gas flows at a controlled flow rate through the first pipe 45a, as the flow of the background gas is controlled or measured by the flowmeter 33. And, when the saturated water-vapor is injected by the injector 31 into inlet 32, the water-vapor is carried through the third pipe 45c to the moisture sensor 35 by diffusion and drifting, and output-responses are obtained by the moisture sensor 35.

Figure 1C:
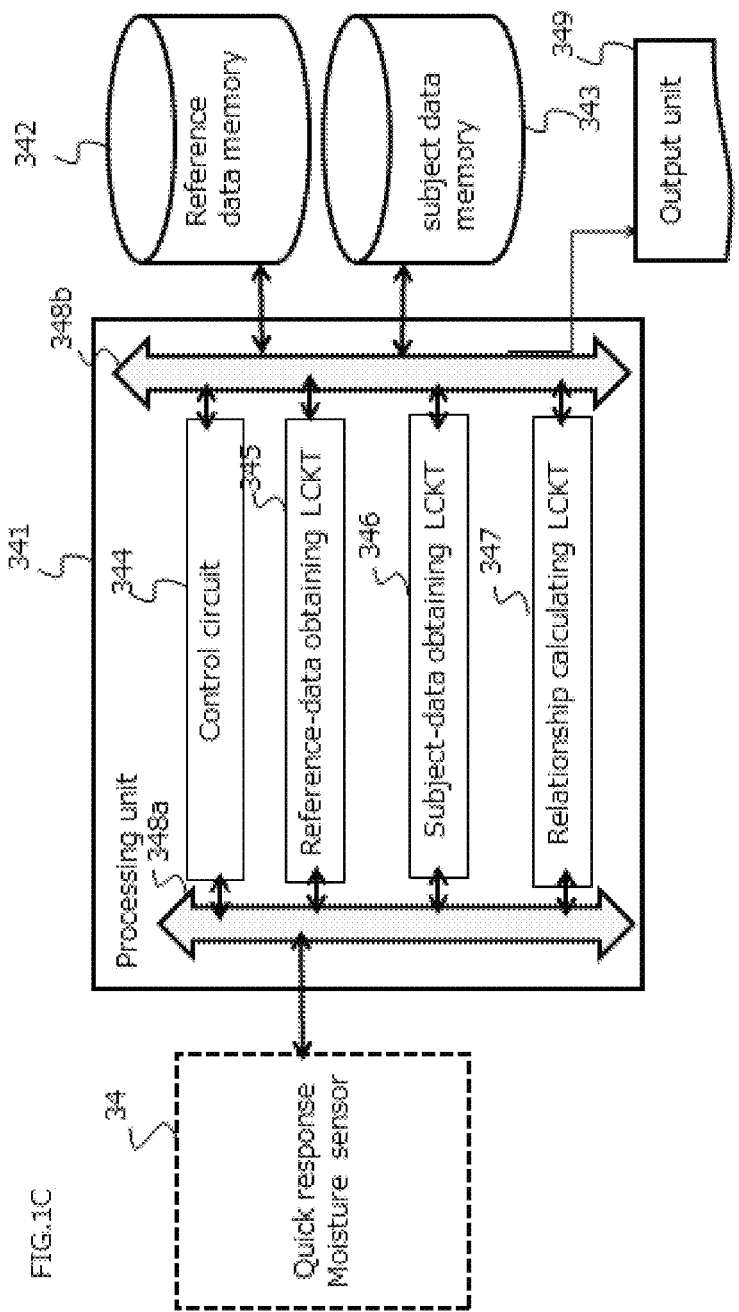
FIG. 1C is an example of a logical structure of a processing unit implementing the dynamic calibration system illustrated in FIG. 1A.

As illustrated in FIG. 1C, the processing unit 341 include a reference-data obtaining logic-circuit (LCKT) 345, a subject-data obtaining logic-circuit (LCKT) 346, a relationship calculating logic-circuit (LCKT) 347 and control circuit configured to control time sequence of the operations of the reference-data obtaining LCKT 345, the subject-data obtaining LCKT 346 and the relationship calculating LCKT 347.

The reference-data obtaining LCKT 345 obtains reference data, which indicate temporal memory of moisture concentrations, after injecting water-vapor with known concentrations into an analyzer of a calibration system. The subject-data obtaining LCKT 346 measures subject data indicating temporal variation of output-responses of a subject sensor element of the analyzer under test, the subject data are obtained under same condition with the reference data was obtained.

The relationship calculating LCKT 347 compares the subject data with the reference data, with same time-duration for obtaining the reference data, the time-duration is measured from a timing at which the water-vapor with the known concentrations is injected. And the relationship calculating LCKT 347 further calculates relationships between the output-responses of the subject sensor element and the known concentrations. The reference data memory 342 stores the reference data obtained by reference-data obtaining LCKT 345. The subject data memory 343 stores the subject data obtained by the subject-data obtaining LCKT 346.

Figure 3:
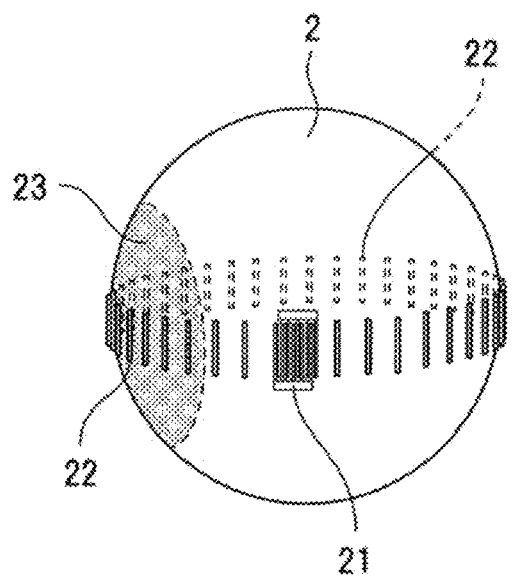
FIG. 3 is a schematic view of an example of a ball SAW sensor.

The moisture sensor 35 is implemented by a ball SAW sensor illustrated in FIG. 3, and the output-responses vary with time owing to the change in moisture concentration. As illustrated in FIG. 3, in the ball SAW sensor implementing the moisture sensor 35, a SAW is excited by the sensor electrode 21 with the specific condition. The SAW generates a naturally collimated beam 22 around the piezoelectric ball 2 so that multiple roundtrips along the equator of the ball can be realized. Since the sensitive film 23 coated on the propagation route of the SAW change the viscoelasticity due to adsorption of water, the concentration of moisture can be evaluated by the attenuation Alpha of the SAW.

The processing unit 341 may be, for example, a central processing unit (CPU) of a computer system. The reference-data obtaining LCKT 345, the subject-data obtaining LCKT 346 and the relationship calculating LCKT 347 may be achieved by functional logical circuits arranged in a general-purpose semiconductor integrated circuit. For example, the processor may include a programmable logic device (PLD) such as a field-programmable gate array (FPGA).

The FPGA is an integrated circuit designed to be configured by a customer or a designer after manufacturing. The FPGA configuration is generally specified using a hardware description language (HDL), similar to that used for an application-specific integrated circuit (ASIC). Similar to the configuration of FPGAs, the processing unit 341 may contain the reference-data obtaining LCKT 345, the subject-data obtaining LCKT 346 and the relationship calculating LCKT 347 as an array of programmable logic blocks.

That is, like software, the electronic hardware of the reference-data obtaining LCKT 345, the subject-data obtaining LCKT 346 and the relationship calculating LCKT 347 can be designed modularly, by creating subcomponents and then higher-level components to instantiate them. In a case where the processing unit 341 is housed in a PC, the output units 349 may be built in the PC, or may be composed integrally with the PC. Meanwhile, in a case where the processing unit 341 is merged with the hybrid IC or module, it is also possible to assemble the processing unit 341 in an inside of the moisture analyzer 34. Alternatively, the reference-data obtaining LCKT 345, the subject-data obtaining LCKT 346 and the relationship calculating LCKT 347 may be implemented by architecture of a software program.

Though not illustrated, in a similar way to a usual computer system, a set of registers, cache memory and a main memory (data memory) as the primary storage, and further a program memory are connected to or built in the processing unit 341 according to the first embodiment of the present invention. The primary storage is directly connected to the processing unit 341 of the calibration system embodied by computer system. The set of registers are internal to the processing unit 341. Registers contain information that the arithmetic and logic unit needs to carry out the current instruction.

Registers are technically the fastest of all forms of computer storage, being switching transistors integrated on the CPU's silicon chip, and functioning as electronic "flip-flops". Cache memory is a special type of internal memory used by processing unit 341 to increase the performance or "throughput". Some of the information in the main memory is duplicated in the cache memory, which is slightly slower but of much greater capacity than the processor registers, and faster but much smaller than main memory.

Although the illustration is omitted, the main memory contains the current data and instructions that are currently being run, and is directly connected to the data bus 348a, 348b. The arithmetic LCKTs 345, 346 and 347 can very quickly transfer information between the set of register and locations in main storage, also known as a "memory addresses".

The program memory can be composed of semiconductor memories, magnetic disks, optical disks, magneto-optical disks, magnetic tapes, and the like. Hence, a calibration program for drive-controlling the reference-data obtaining LCKT 345, the subject-data obtaining LCKT 346 and the relationship calculating LCKT 347, which are illustrated in FIG. 1, and causing the LCKTs 345, 346, 347 to calibrating the moisture sensor, according to the first embodiment just needs to be stored in the program memory (not illustrated) of a computer system that implements the moisture analyzer34. Meanwhile, varieties of input/output data and parameters, which are necessary for calibration, data under computation, and the like, can be stored in the data memory such as SRAM.

The processing unit 341 according to the first embodiment of the present invention is configurable of the computer system such as the PC, and accordingly, illustration of the PC is omitted. However, the processing unit 341 may further include input units such as a PC keyboard, a mouse, and a light pen. Specifically, the mouse is clicked for the operator notation displayed on the output units 349, whereby measurement conditions or sensor specifications can be entered. Moreover, as another output unit, a printer device or the like may be provided as well as the output units 349 illustrated in FIG. 1C.

According to the calibration system pertaining to the first embodiment, the effectiveness such that a measurement time as short as ten minutes can be achieved, while ten hours are required for static calibration pertaining to the illustrative examples. Since the calibration system pertaining to the first embodiment implemented by a small number of simple components, it is possible to downsize the scale of the calibration system, and apply the calibration system to on-site calibration. Moreover, since the calibration system pertaining to the first embodiment uses saturated water-vapor as calibration gases, it is easy to prepare high precision calibrated gases in the field without a detailed control.

Dynamic Calibration System

Figure 7:
FIG. 7 is a photograph illustrating gas bag for saturated water-vapor generator and gas-tight syringe as injector.

As the water-vapor generator 36 illustrated in FIG. 1B, we use a sampling gas bag for gas analysis, whose inner surface was inactivated, as illustrated in FIG. 7. After purging the gas bag with nitrogen gas, pure water is injected into the bag and the bag is saturated with water-vapor at room temperature controlled by an air conditioner. As the injector 31 illustrated in FIGS. 1A and 1B, we use a gas-tight syringe, with which we can control the injection volume using the scale of the syringe. The saturated water-vapor is extracted from the gas bag using the gas-tight syringe serving as the injector 31, and injected into the inlet 32 provided 170 mm upstream of the ball SAW sensor as the moisture sensor 35 connected to the third pipe 45c. The nitrogen gas flow through the first pipe 45a, the second pipe 45b and third pipe 45c is controlled using a mass flow controller as the flow meter 33.

We installed a ball SAW sensor as the moisture sensor 35 in the system pertaining to the first embodiment, and measured responses by injection of saturated water-vapor. The injection volume was 1 ml and the flow rate of the background gas was 100 ml·min$^{-1}$. At the measurement, the room temperature was 21.6 degrees centigrade. Response time was evaluated as the time within which a 10% to 90% increase in the FP was observed after the injection of saturated water-vapor.

Figure 8A:
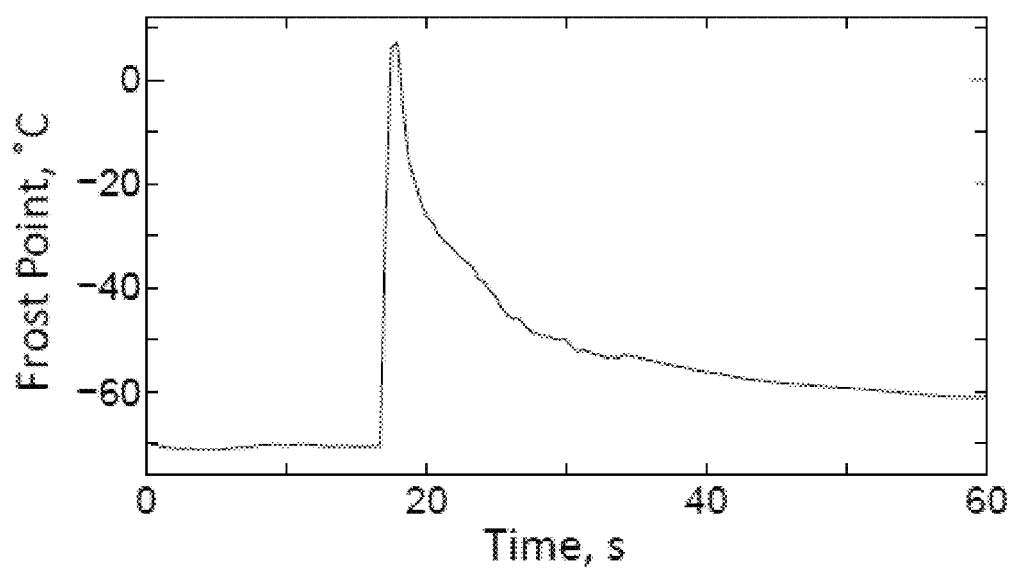
FIG. 8A is a diagram illustrating temporal variation of FP measured by ball SAW trace moisture analyzer.

FIG. 8A illustrates a temporal variation of the FP due to the injection of saturated water-vapor measured using the moisture sensor 35. The FP increased immediately after injection and then decreased gradually. The decrease took about ten minutes and is considered to represent a process at which the water adsorbed on the pipe surface was gradually desorbed.

Figure 8B:
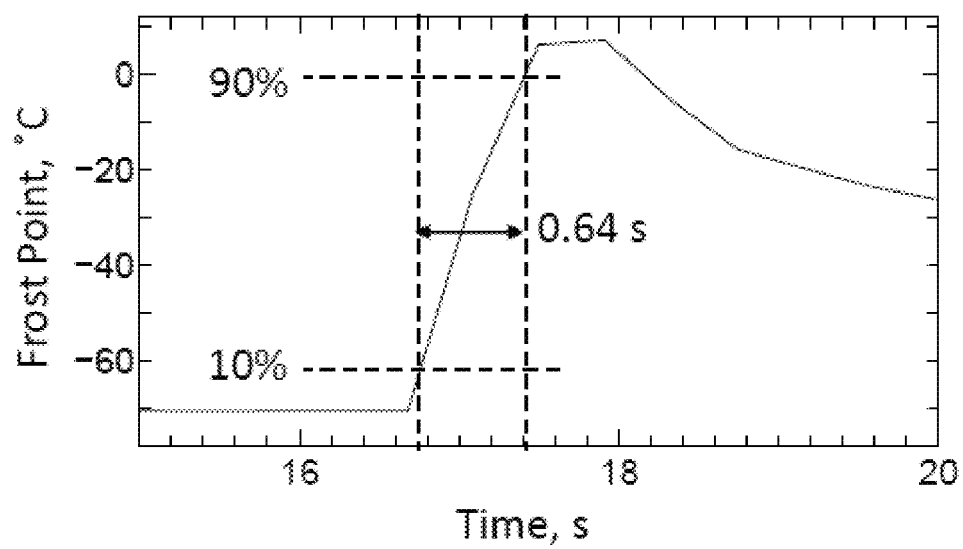
FIG. 8B is a diagram enlarging the range of time from 15 to 20 seconds in FIG. 8A.

The expanded view of the peak is illustrated in FIG. 8B. The response time taken for 10% to 90% of the FP change from −70 to 10 degrees centigrade was only 0.64 s. Since the response time is less than one second, it can be regarded that the equilibrium between the moisture concentration within the sensitive film and that in the atmosphere is rapidly reached at any instance of the dynamic calibration process pertaining to the first embodiment, which takes ten minutes. This rapid equilibrium is the basis for the validity of the dynamic calibration process pertaining to the first embodiment.

Dynamic Calibration Method

First, to obtain a reference data for a dynamic calibration method pertaining to the first embodiment, we install a reference sensor element implemented by the ball SAW sensor as the moisture sensor 35 illustrated in FIG. 1A. In Step 11 of the procedure illustrated in FIG. 2 the reference-data obtaining LCKT 345 obtains reference data, which indicate temporal variation of moisture concentrations, after injecting water-vapor, which has known concentrations, into an analyzer under test.

The reference sensor element has been already calibrated by the static calibration method pertaining to the illustrative example, which has been illustrated in FIG. 4. The calibration system may be the dynamic calibration system pertaining to the first embodiment. Then, the calibration system measures the temporal variation of the attenuation Alpha by the injection of saturated water-vapor. The temporal variation of the FP can be obtained by substituting the attenuation Alpha at each time in Eq. (4). The reference-data obtaining LCKT 345 stores the obtained reference data into the reference data memory 342.

Figure 9A:
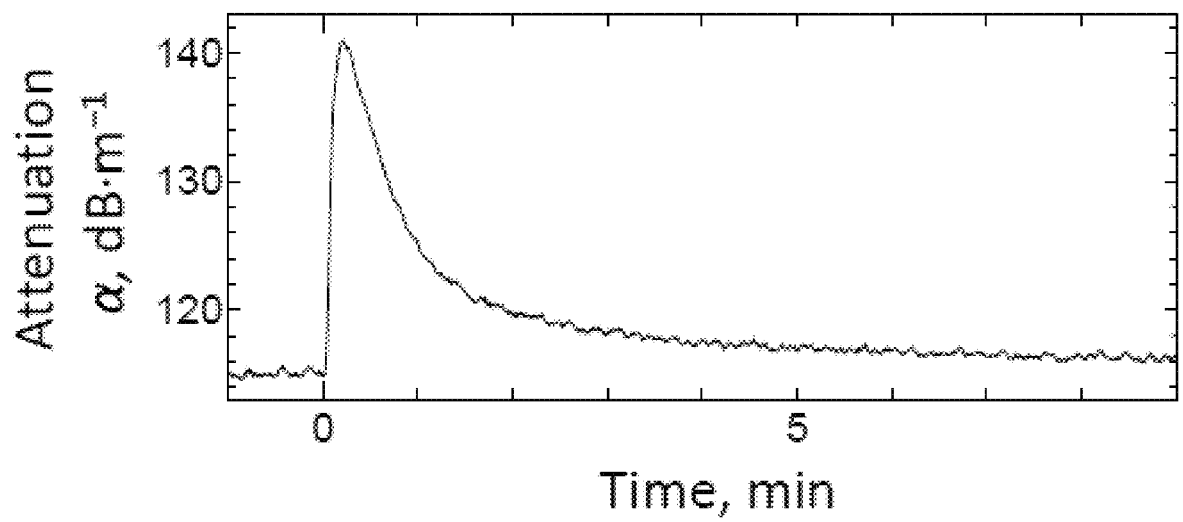
FIG. 9A is a diagram illustrating a temporal variation of attenuation of SAW after injection of saturated water-vapor.
Figure 9B:
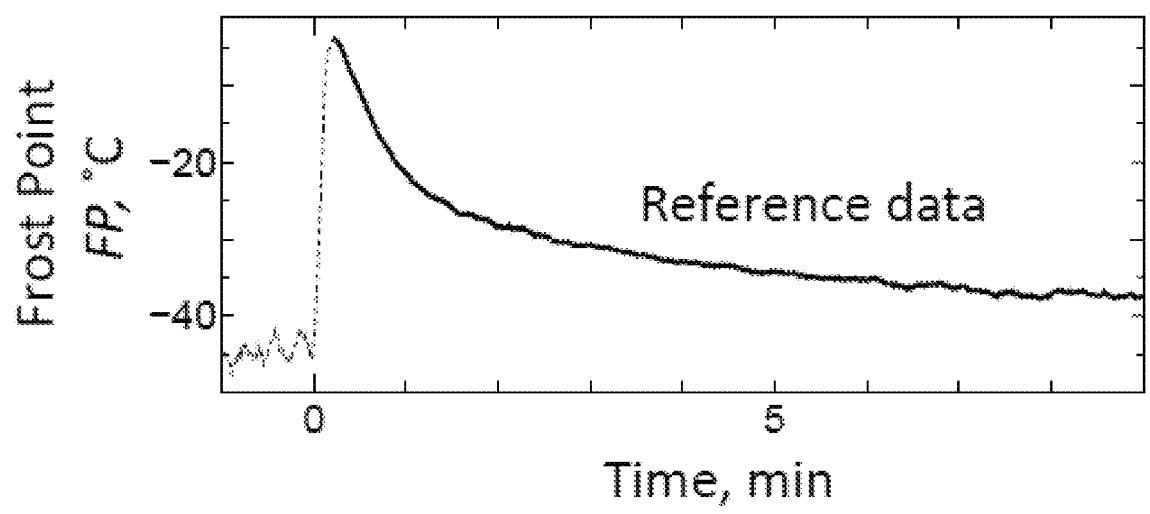
FIG. 9B is a diagram illustrating reference data, that illustrates a temporal variation of FP calculated using calibration curve determined by static calibration.

The measurement result for the reference data is illustrated in FIGS. 9A and 9B at a background gas flow rate of 10 ml·min$^{-1}$, a saturated water-vapor injection volume of 1 ml, and a room temperature of 21 degrees centigrade. From the temporal variation of the attenuation Alpha after the injection of saturated water-vapor, as illustrated in FIG. 9A, the temporal variation of FP was obtained using the calibration curve obtained using Eq. (4), as illustrated in FIG. 9B. Since the rising part of the peak changes rapidly, the rising part is not used for the calibration, and the gradually decreasing part of the curve illustrated in solid curve is used as reference data.

Figure 2:
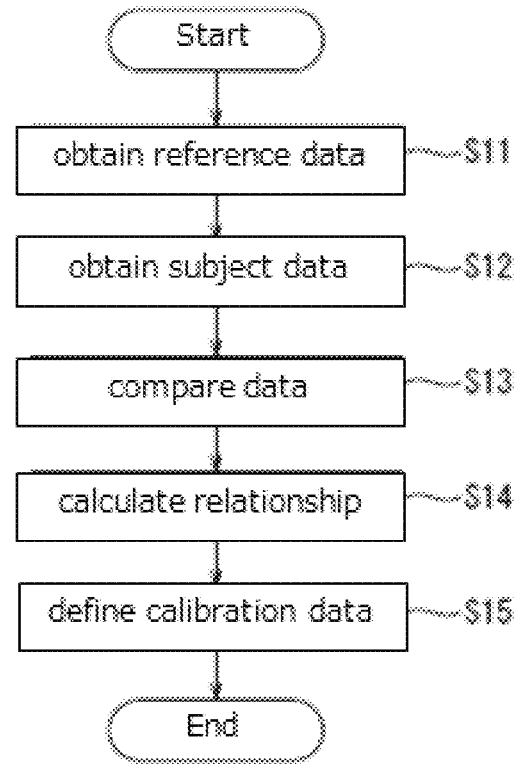
FIG. 2 is an example of a flowchart illustrating a flow of a procedure of a dynamic calibration method pertaining to a first embodiment.
Figure 10A:
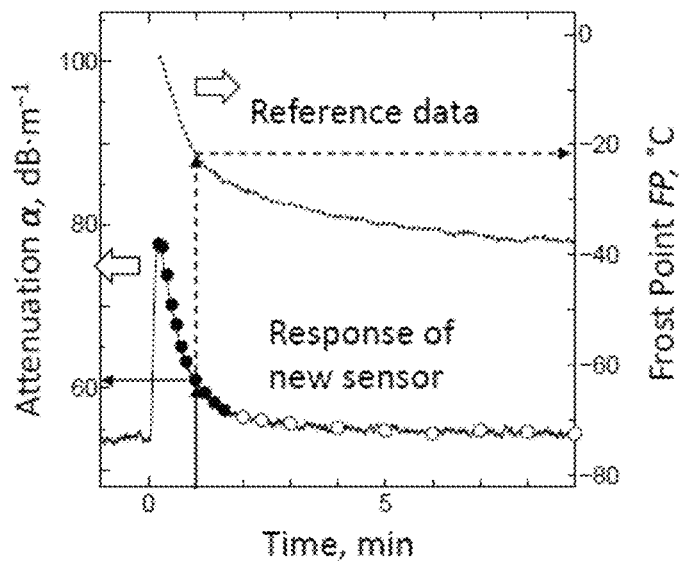
FIG. 10A is a diagram illustrating reference data and output-response of subject sensor element.

Next, the reference sensor element is replaced with a subject sensor element to be calibrated, In Step 12 of the procedure illustrated in FIG. 2 the subject-data obtaining LCKT 346 measures subject data indicating temporal variation of output-responses of a subject sensor element of an analyzer under test, the subject data are obtained under same condition with the reference data was obtained. For example, the temporal variation of the attenuation Alpha is measured for ten minutes under the same conditions as the condition when the reference data was measured. The subject sensor element is implemented by the ball SAW sensor. The subject-data obtaining LCKT 346 stores the obtained subject data into the subject data memory 343. The attenuation Alpha of a new sensor—or the subject moisture sensor—under the same condition as the measurement for the reference data is illustrated by the solid curve in FIG. 10A.

In Step 13 of the procedure illustrated in FIG. 2, the relationship calculating LCKT 347 reads out the reference data from the reference data memory 342, and furthermore, the relationship calculating LCKT 347 reads out the subject data from the subject data memory 343. Thereafter, the relationship calculating LCKT 347 compares the subject data with the reference data, with same time-duration for obtaining the reference data, the time-duration is measured from a timing at which the water-vapor with the known concentrations is injected.

And, furthermore, in Step 14 of the procedure illustrated in FIG. 2, the relationship calculating LCKT 347 further calculates relationships between the output-responses of the subject sensor element and the known concentrations.

Figure 10B:
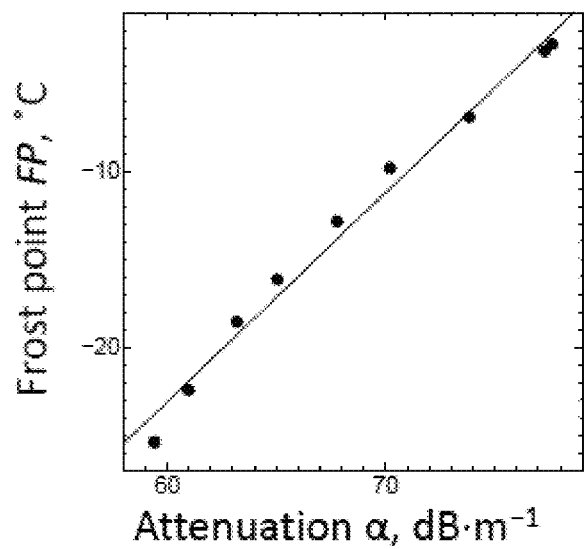
FIG. 10B is a diagram illustrating relationship between attenuation Alpha and FP in high concentration range.

Using the reference data illustrated by the dotted curve at same time-duration, we obtained the FP at the right ordinate. FIG. 10B illustrates the relationship between the attenuation Alpha and the FP in the high concentration range as illustrated by closed circles.

Figure 10C:
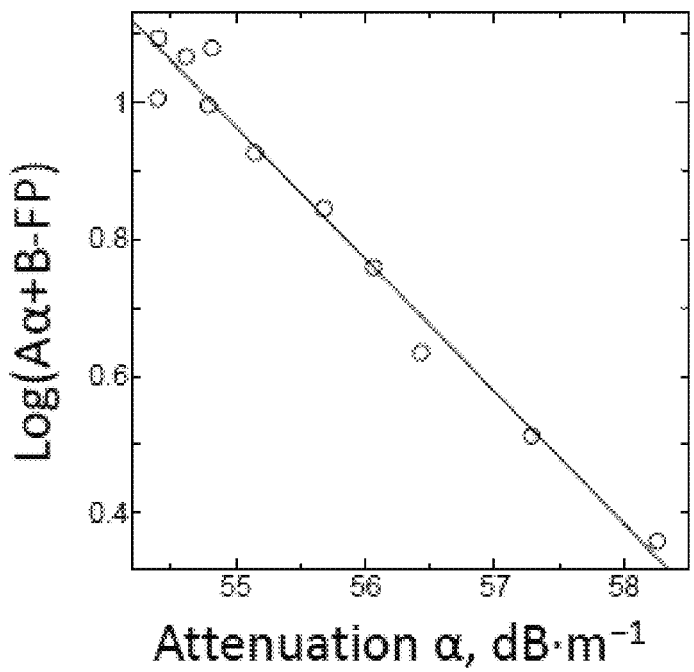
FIG. 10C is a diagram illustrating relationship between the attenuation Alpha and FP in low concentration range.

Since the relationship illustrated in FIG. 10B is almost linear, the coefficients of calibration curves A and B were determined to be A=1.188 and B=−94.41 by a least squares fitting. On the other hand, FIG. 10C illustrates the relationship between the attenuation Alpha and the values obtained by the functional expression represented on the left-hand side of Eq. (3) in the low concentration range as illustrated by open circles. Since the relationship illustrated in FIG. 10C is also linear, coefficients C and D were determined to be C=−0.1983 and D=11.88 by a least squares fitting.

In Step 15 of the procedure illustrated in FIG. 2, the relationship calculating LCKT 347 further defines the calibration data. That is, the calibration curve of the new sensor element obtained by the dynamic calibration method is given by

[Math. 5]

$$FP=1.188\alpha-94.41-10^{-0.1983\alpha+11.88}. \quad (5)$$

The calibration curve of the subject sensor element is derived as the relationship between the attenuation Alpha and the FP of the reference data at same time-duration.

The relationship calculating LCKT 347 further send the defined calibration data toward the output unit 349. Alternatively, the defined calibration data may be stored in a calibration data memory, although the illustration of the calibration data memory is omitted.

Finally, the subject sensor element is calibrated again by the static calibration method. The calibration curve of the same subject sensor element obtained by the static calibration method is given by

[Math. 6]

$$FP=1.257\alpha-101.3-10^{-0.1994\alpha+11.86}. \quad (6)$$

and the calibration curve obtained is compared with that obtained by the dynamic calibration method pertaining to the first embodiment.

Figure 11:
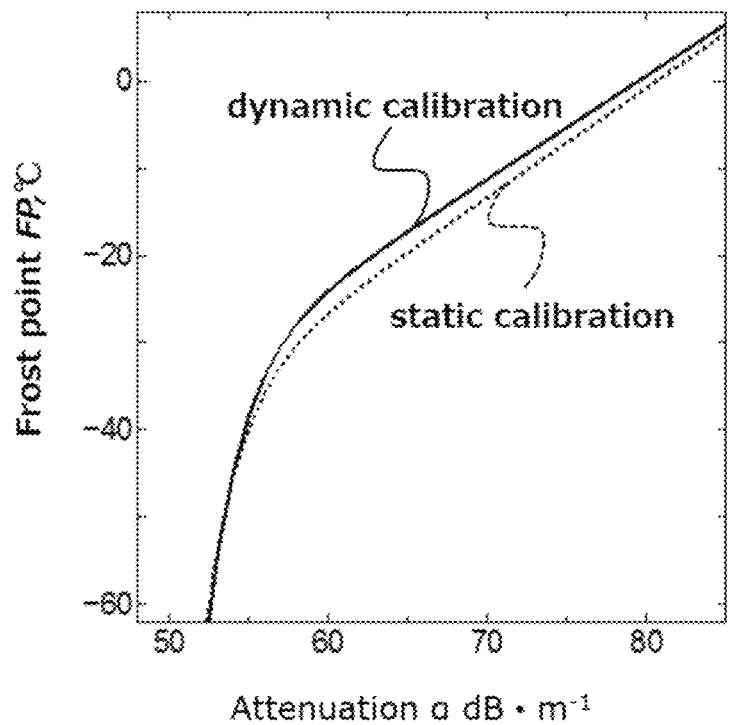
FIG. 11 is a diagram illustrating calibration curves obtained by the dynamic calibration method pertaining to the first embodiment and the static calibration method pertaining to the illustrative example.

In FIG. 11, the result of dynamic calibration curve using Eq. (5) is illustrated as a solid curve and the result of static calibration curve using Eq. (6) is illustrated as a dotted curve. These two curves look nearly identical.

Figure 12:
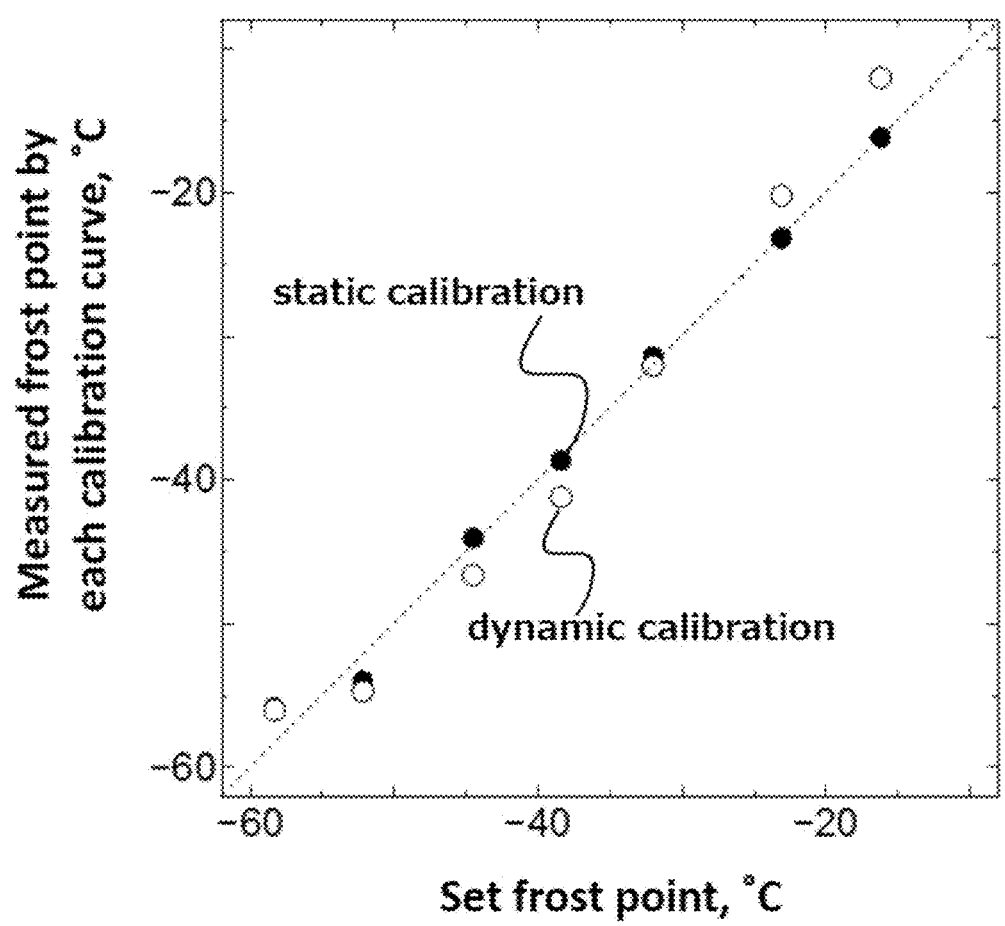
FIG. 12 is a diagram illustrating relationships between set FP and measured FP determined using the dynamic calibration method pertaining to the first embodiment and earlier calibration curves obtained by the static calibration method pertaining to the illustrative example.

FIG. 12 illustrates the error between the set FP and the measured FP calculated by the substitution of the attenuation Alpha into each calibration curve. The abscissa illustrates the set FP and the ordinate illustrates the measured FP. If there is no error, the measured FP should be plotted on the 45 degrees line illustrated by the dotted line. Open circles illustrate results obtained by the dynamic calibration and closed circles illustrate those obtained by the static calibration. In the FP range from −59 to −17 degrees centigrade, the root-mean-square (RMS) errors of the static and dynamic calibration methods were 0.88 degrees centigrade and 2.12 degrees centigrade, respectively.

The RMS error of 2.12 degrees centigrade of the dynamic calibration in the FP range from −59 to −17 degrees centigrade is acceptable for a rough estimate of the sensor condition. Since this error is considered to be the accumulation of errors in the calibration curve obtained using Eq. (4) acquired as the reference data, errors in the amount of injected saturated water-vapor as the calibration gas, and subtle differences in temperature and atmospheric pressure, it can be reduced by improving the system components.

According to the dynamic calibration method pertaining to the first embodiment, the effectiveness such that a measurement time as short as ten minutes can be achieved, while ten hours are required for static calibration pertaining to the illustrative examples. Therefore, it is possible to apply the dynamic calibration method to on-site calibration. Moreover, since the dynamic calibration method pertaining to the first embodiment uses saturated water-vapor as calibration gases, it is easy to prepare high precision calibrated gases in the field without a detailed control.

Calibration Program

For example, the calibration program according to the first embodiment of the present invention is stored in a non-transitory computer readable storage medium, and the program memory of the processing unit 341 is caused to read a content recorded in the external recording medium, whereby the calibration program concerned can execute a series of processing of the calibration of the present invention.

Namely, the calibration program, which causes the processing unit 341 in the calibration system pertaining to the first embodiment to execute processing for calibration, includes a series of instructions for performing the procedure of the calibration. The series of instructions may include instructions to the reference-data obtaining LCKT 345 so that the reference-data obtaining LCKT 345 obtains reference data, which indicate temporal variation of moisture concentrations, after injecting water-vapor with known concentrations into an analyzer of a calibration system.

The series of instructions further includes instructions to the subject-data obtaining LCKT 346 so that the subject-data obtaining LCKT 346 measures subject data indicating temporal variation of output-responses of a subject sensor element of an analyzer under test, the subject data are obtained under same condition with the reference data was obtained The series of instructions still further includes instructions to the relationship calculating LCKT 347 so that compares the subject data with the reference data, with same time-duration for obtaining the reference data, the time-duration is measured from a timing at which the water-vapor with the known concentrations is injected, The series of instructions yet still further includes instructions to the relationship calculating LCKT 347 so that the relationship calculating LCKT 347 calculates relationships between the output-responses of the subject sensor element and the known concentrations.

Here, the "non-transitory computer readable storage medium" means such a medium that can record a program. The non-transitory computer readable storage medium includes, for example, an external memory device of a computer, a semiconductor memory, a magnetic disk, an optical disk, a magneto-optical disk, a magnetic tape, and the like. Specifically, a flexible disk, a CD-ROM, an MO disk, an open-reel tape and the like are included in the "non-transitory computer readable storage medium".

For example, a main body of the processing unit 341 can be configured to build therein a flexible disk device and an optical disk device or to cause the flexible disk device and the optical disk device to be externally connected thereto. The flexible disk is inserted into the flexible disk drive from an insertion slot thereof and the CD-ROM is inserted into the optical disk drive from an insertion slot thereof and both of them are subjected to a predetermined reading operation, whereby the programs stored in these external recording mediums can be installed into the program memory that implements the processing unit 341.

Moreover, a predetermined drive device is connected to the processing unit 341, whereby, for example, the ROM and the magnetic tape device can be used as external recording mediums. Furthermore, it is possible to store the calibration program in the program memory via an information processing network such as the Internet in place of using the external recording medium.

According to the calibration program pertaining to the first embodiment, the effectiveness such that a measurement time as short as ten minutes can be achieved, while ten hours are required for static calibration pertaining to the illustrative examples. Therefore, it is possible to apply the calibration program to on-site calibration. Moreover, it is easy to prepare high precision calibrated gases in the field without a detailed control.

Second Embodiment

Figure 13:
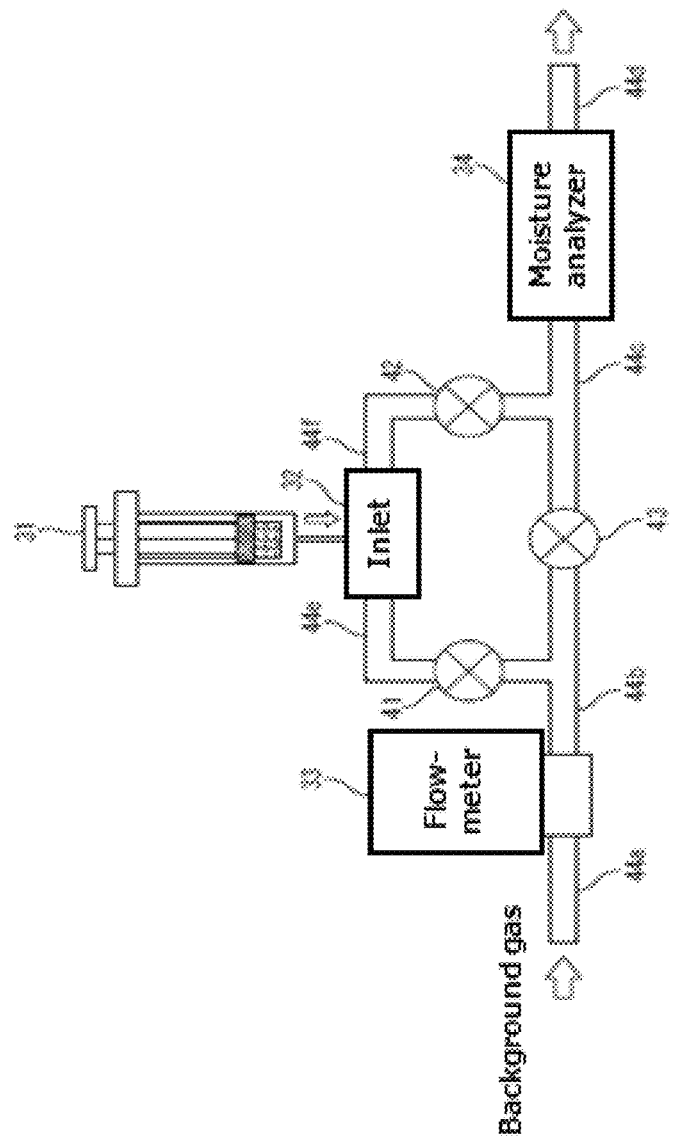
FIG. 13 is a conceptual diagram of a calibration system pertaining to a second embodiment of the present invention.

As illustrated in FIG. 13, a calibration system pertaining to a second embodiment of the present invention encompasses a first pipe 44a through which background gas flows, a flowmeter 33 installed between the first pipe 44a and a second pipe 44b. The second pipe 44b is branched into a first branched pipe 44e having a first valve 41, and another branch of the second pipe 44b is connected to a third pipe 44c via a second valve 43.

The third pipe 44c is branched into a second branched pipe 44f having a third valve 42, and another branch of the third pipe 44c is connected to a moisture analyzer 34, and therefore the third pipe 44c serve as "an introduction pipe" for the moisture analyzer 34. In the calibration system pertaining to the second embodiment further encompasses an inlet 32 installed between the first branched pipe 44e and the second branched pipe 44f and an injector 31 for injecting a constant volume of the calibration gas to the inlet 32.

By branching the pipe at upstream and downstream of the inlet 32 and switching the flow path using the first valve 41, the second valve 43 and the third valve 42, it is possible to adopt configuration which allows replacement and maintenance of the inlet 32 on-line, as the moisture analyzer 34 is installed at downstream of the inlet 32 through the third pipe 44c.

The water-vapor generator 36, which was illustrated in FIG. 1B in the explanation of the first embodiment, produces the saturated water-vapor in background gases on the head space of water, the water is contained in the lower portion of the water-vapor generator 36. Prior to conducting calibration with the calibration system illustrated in FIG. 13, the tip of the injector 31 is supposed to be inserted in the water-vapor generator 36. And, by the injector 31, the saturated water-vapor is sampled from the water-vapor generator 36.

Thereafter, the background gas is introduced into the first pipe 44a illustrated in FIG. 13, and the background gas flows at a controlled flow rate through the first pipe 44a, as the flow of the background gas is controlled or measured by the flowmeter 33. And, when the saturated water-vapor is injected by the injector 31 into inlet 32, the water-vapor is carried through the third pipe 45c to the moisture analyzer 34 by diffusion and drifting, and output-responses are obtained by the moisture analyzer 34.

The moisture analyzer 34 is implemented by a ball SAW sensor illustrated in FIG. 3 as the moisture sensor 35 of the first embodiment, and the output-responses vary with time owing to the change in moisture concentration. Although the illustration is omitted, similar to the configuration explained in the first embodiment, the moisture analyzer 34 further includes the processing unit 341, the reference data memory 342 and the subject data memory 343.

And, the processing unit 341 encompasses the reference-data obtaining LCKT 345, the subject-data obtaining LCKT 346 and the relationship calculating LCKT 347, which are explained in the first embodiment. Since the calibration system pertaining to the second embodiment embraces simple components, it is possible to downsize the calibration system, and apply the calibration system to on-site calibration. Moreover, since the calibration system pertaining to the second embodiment uses saturated water vapor as calibration gases, it is easy to prepare high precision calibrated gases in the field without a detailed control.

According to the calibration system pertaining to the second embodiment, the effectiveness such that a measurement time as short as ten minutes can be achieved, while ten hours are required for static calibration pertaining to the illustrative examples. Since the calibration system pertaining to the second embodiment implemented by a small number of simple components, it is possible to downsize the scale of the calibration system, and apply the calibration system to on-site calibration. Moreover, since the calibration system pertaining to the second embodiment uses saturated water-vapor as calibration gases, it is easy to prepare high precision calibrated gases in the field without a detailed control.

When the injected water concentration is $C_W$ and the injection volume is $V_S$, total injected water content $V_W$ is given by $$V_W = C_W V_s \quad (7)$$

On the other hand, the water vapor injected into the pipe with the background gases passing through at the flow rate $F_0$, diffuses in the flow direction and reaches the sensor while adsorbed to/desorbed from the pipe wall surface, so the moisture concentration around the sensor changes with the time. Since concentration integration $I_C$ is the time integral of response curve $C_m(t)$ $$I_C = \int C_m(t) dt \quad (8),$$

and, the product of the concentration integration $I_C$ and the gas flow rate $F_0$ equals to $V_W$, the concentration integration $I_C$ is given by $$I_C = V_W / F_0 \quad (9).$$

Figure 14A:
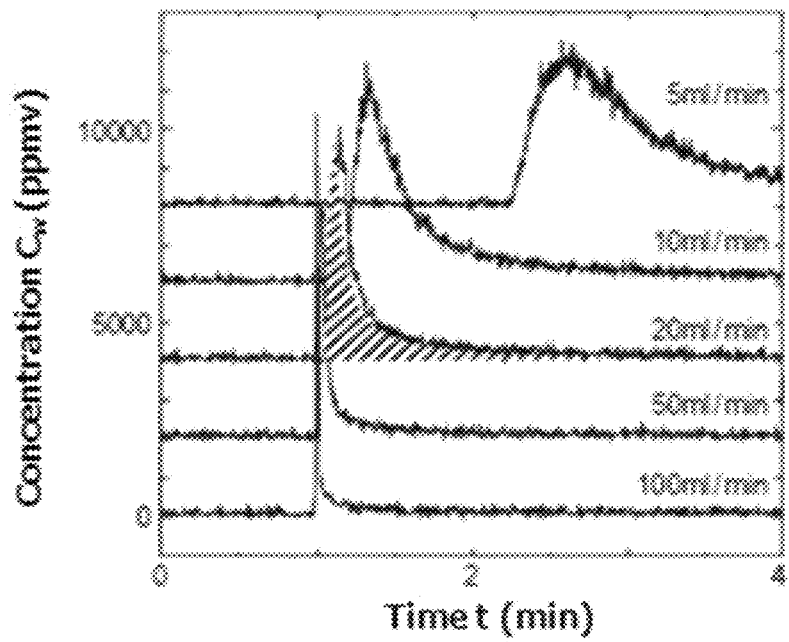
FIG. 14A is a diagram illustrating temporal variation of moisture concentration by injection of saturated water vapor obtained by a calibration system pertaining to the second embodiment.

In a condition that the boll SAW sensor illustrated in FIG. 3 is connected to the calibration system pertaining to the second embodiment, saturated water vapor gas was injected in the calibration system. The flow rate of background gas was changed to 5, 10, 20, 50, and 100 mL/min using a mass flow controller. FIG. 14A illustrates a temporal variation of moisture concentration calculated from the output-responses of the ball SAW sensor. Each of the output-responses is plotted after shifted by 2000 ppmv. The moisture concentration of injected calibration gas was calculated as CW=28100 ppmv from the saturated water vapor pressure at room temperature of 23 degrees centigrade.

Figure 14B:
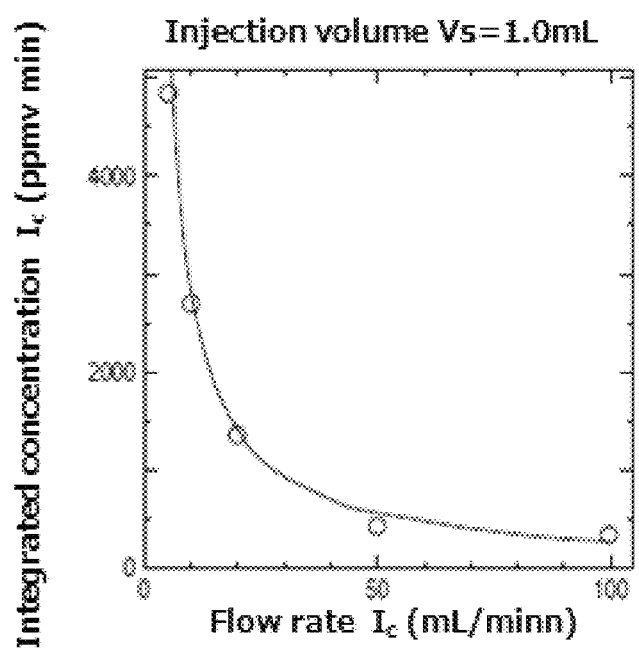
FIG. 14B is a diagram illustrating relationship between integrated concentration and flow rate of background gas obtained by the calibration system pertaining to the second embodiment.

When the gas flow rate is 10 mL/min, the total moisture content is 0.0281 mL from Eq. (7), and the theoretical value of concentration integration $I_C$ is 2810 ppm min from Eq. (9). The value of 2810 ppm min is almost equal to $I_C$=2694 ppm min obtained from the response curve by Eq. (8). FIG. 14B illustrates the result of carrying out similar measurement at each flow rate. The measured values at all flow rates, which are indicated by open circles, almost agreed with the theoretical values indicated by the solid curve. Consequently, it was illustrated that operation of the calibration system pertaining to the second embodiment follows the theoretical prediction.

Therefore, a similar method for calibration of moisture sensor as the dynamic calibration method pertaining to the first embodiment can be executed. That is, the dynamic calibration method pertaining to the second embodiment includes the step of the reference-data obtaining LCKT 345 obtains reference data, which indicate temporal variation of moisture concentrations, after injecting water-vapor with known concentrations into an analyzer of a calibration system. And, the dynamic calibration method pertaining to the second embodiment includes the step of the subject-data obtaining LCKT 346 measures subject data indicating temporal variation of responses of a subject sensor element of an analyzer under test, the subject data are obtained under same condition with the reference data was obtained.

Furthermore, the dynamic calibration method pertaining to the second embodiment includes the step of the relationship calculating LCKT 347 comparers the subject data with the reference data, with same time-duration for obtaining the reference data, the time-duration is measured from a timing at which the water-vapor with the known concentrations is injected. Furthermore, the dynamic calibration method pertaining to the second embodiment includes the step of the relationship calculating LCKT 347 calculates relationships between the responses of the subject sensor element and the known concentrations.

According to the dynamic calibration method pertaining to the second embodiment, the effectiveness such that a measurement time as short as ten minutes can be achieved, while ten hours are required for static calibration pertaining to the illustrative examples. Therefore, it is possible to apply the dynamic calibration method to on-site calibration. Moreover, since the dynamic calibration method pertaining to the second embodiment uses saturated water-vapor as calibration gases, it is easy to prepare high precision calibrated gases in the field without a detailed control.

According to the calibration program pertaining to the second embodiment, the effectiveness such that a measurement time as short as ten minutes can be achieved, while ten hours are required for static calibration pertaining to the illustrative examples. Therefore, it is possible to apply the calibration program to on-site calibration. Moreover, it is easy to prepare high precision calibrated gases in the field without a detailed control.

The dynamic calibration method can be executed by the processing unit 341 by a calibration program pertaining to the second embodiment, which is essentially same as the calibration program pertaining to the first embodiment. Therefore, duplicated explanation of the calibration program is omitted. And, a series of instructions for performing the dynamic calibration method shall be stored in a non-transitory computer readable storage medium.

Other Embodiments

Various modifications will become possible for those skilled in the art after receiving the teaching of the present disclosure without departing from the scope thereof. The present invention can be applied to on-site calibration not only of a moisture analyzer using a ball SAW sensor but also of other moisture analyzers. It is also effective as a calibration method of a moisture analyzer applied to processes using special gases for which there is no applicable calibration system.

Also, the calibration method pertaining to the first and second embodiment can be easily applied not only to moisture analyzers, but also to analyzers of other gases such as alcohol, acid and aldehyde.

In this way the present invention includes inherently the various embodiments, which are not described here. Therefore, technical scopes of the present invention are prescribed only by the description of claims, being proper from the above explanation.

What is claimed:

1. A system for calibrating a moisture sensor comprising a processing unit, the processing unit including:
   a logic circuit configured to obtain reference data, which indicate temporal variation of moisture concentrations, after injecting water-vapor with known concentrations into an analyzer;
   a logic circuit configured to measure subject data indicating temporal variation of output-responses of a subject sensor element of the analyzer under test, the subject data are obtained under the same condition with the reference data was obtained;
   a logic circuit configured to compare the subject data with the reference data, with same time-duration for obtaining the reference data, the time-duration is measured from a timing at which the water-vapor with the known concentrations is injected for calculating relationships between the output-responses of the subject sensor element and the known concentrations;

an injector configured to inject a constant volume of a calibration gas;

an inlet configured to receive a tip of the injector;

a flowmeter configured to control a flow rate of a background gas;

a moisture sensor configured to accept the subject sensor element, an output of the moisture sensor is connected to the processing unit;

a first pipe for introducing the background gas to the flowmeter;

a second pipe connecting the flowmeter with the inlet, configured to flow the background gas at a controlled flow rate by the flowmeter; and a third pipe connecting the inlet with the moisture sensor, configured to introduce the background gas and the calibration gas into the moisture sensor.

2. The system of claim 1, further comprising:

a saturated water-vapor generator configured to generate a calibration gas, which is saturated with water-vapor in the background gas, wherein the tip of the injector is inserted in the saturated water-vapor generator so as to sample the calibration gas with the constant volume, prior to a timing when the tip is inserted in the inlet.

3. The system of claim 2, wherein the subject sensor element is a ball SAW sensor.

4. A method for calibration of moisture sensor, including:

obtaining reference data, which indicate temporal variation of moisture concentrations, after injecting water-vapor with known concentrations into an analyzer of a calibration system;

measuring subject data indicating temporal variation of output-responses of a subject sensor element of the analyzer under test, the subject data are obtained under same condition with the reference data was obtained;

comparing the subject data with the reference data, with same time-duration for obtaining the reference data, the time-duration is measured from a timing at which the water-vapor with the known concentrations is injected; and calculating relationships between the output-responses of the subject sensor element and the known concentrations;

inserting a tip of the injector into a saturated water-vapor generator so as to sample a calibration gas at a constant volume; and inserting the tip of the injector into an inlet of the system configured to introduce the calibration gas to the subject sensor element.

5. A non-transitory computer readable storage medium storing a calibration program of system for calibrating a moisture sensor, the calibration program causing a processing unit in the system to execute processing for calibration by a series of instructions for performing calibration, comprising:

obtaining reference data, which indicate temporal variation of moisture concentrations, after injecting water-vapor with known concentrations into an analyzer of a calibration system;

measuring subject data indicating temporal variation of output-responses of a subject sensor element of the analyzer under test, the subject data are obtained under same condition with the reference data was obtained;

comparing the subject data with the reference data, with same time-duration for obtaining the reference data, the time-duration is measured from a timing at which the water-vapor with the known concentrations is injected;

calculating relationships between the output-responses of the subject sensor element and the known concentrations;

inserting a tip of the injector into a saturated water-vapor generator so as to sample a calibration gas at a constant volume; and inserting the tip of the injector into an inlet of the system configured to introduce the calibration gas to the subject sensor element.

* * * * *